(12) United States Patent
Pernot (10) Patent No.: US 8,992,491 B2
(45) Date of Patent: Mar. 31, 2015

(54) WOUND DRESSING INCLUDING AGGLOMERATES OF PARTICLES SUITABLE FOR RAPIDLY GELLING OR SOLUBILIZING

(75) Inventor: Jean-Marc Pernot, Dijon (FR)

(73) Assignee: Laboratoires Urgo, Chenove (FR)

( * ) Notice: Subject to any disclaimer, the term of this patent is extended or adjusted under 35 U.S.C. 154(b) by 0 days.

(21) Appl. No.: 13/521,147

(22) PCT Filed: Jan. 13, 2011

(86) PCT No.: PCT/FR2011/050062
§ 371 (c)(1),
(2), (4) Date: Oct. 1, 2012

(87) PCT Pub. No.: WO2011/086329
PCT Pub. Date: Jul. 21, 2011

(65) Prior Publication Data
US 2013/0018335 A1   Jan. 17, 2013

(30) Foreign Application Priority Data

Jan. 14, 2010 (FR) ...................................... 10 50221

(51) Int. Cl.
*A61F 13/02* (2006.01)
*A61L 15/58* (2006.01)

(52) U.S. Cl.
CPC *A61L 15/58* (2013.01); *A61F 13/02* (2013.01)
USPC .......................................... 604/307; 604/543

(58) Field of Classification Search
CPC ....... A61F 13/00; A61F 13/02; A61F 13/022; A61F 13/0225; A61F 13/0253; A61F 13/0256
USPC .......................... 604/307, 540–543
See application file for complete search history.

(56) References Cited

U.S. PATENT DOCUMENTS 3,598,123 A * 8/1971 Zaffaroni ....................... 424/435
3,742,951 A * 7/1973 Zaffaroni ....................... 424/434

(Continued)

FOREIGN PATENT DOCUMENTS

CN    101569758    11/2009
EP    0264299      4/1988

(Continued)

OTHER PUBLICATIONS

Satas: "Handbook of Pressure Sensitive Technology", 3rd edition, 1999, pp. 346 to 398 (Article by Jagisch et al.).

*Primary Examiner* — Philip R Wiest
*Assistant Examiner* — Benjamin Klein
(74) *Attorney, Agent, or Firm* — Hamre, Schumann, Mueller & Larson, P.C.

(57) ABSTRACT

The present invention relates to a bandage including an adhesive hydrocolloid mass, wherein said bandage includes, on at least one portion of the surface of the adhesive mass intended for being in contract with the wound when the bandage is being used, a plurality of agglomerates made up of particles linked to one another, preferably in a multi-layer configuration, at least 90% and preferably at least 95% of said particles being made up of one (or more) material(s) selected among polysaccharides, proteins and synthetic polymers, and being suitable for solubilizing or gelling in under ten seconds, and preferably still in less than one second when in contact with the exudate from the wound. The bandage according to the invention is intended for treating wounds such as blisters, exuding wounds, burns and dermal-epidermal lesions, whether superficial, deep, chronic or acute.

22 Claims, 2 Drawing Sheets

(56) References Cited

U.S. PATENT DOCUMENTS

| | | | |
|---|---|---|---|
| 4,231,369 A | 11/1980 | Sorensen et al. | |
| 4,367,732 A | 1/1983 | Poulsen et al. | |
| 5,653,699 A * | 8/1997 | Reed et al. | 604/307 |
| 5,681,305 A | 10/1997 | Korpman | |
| 6,051,748 A | 4/2000 | Auguste et al. | |
| 6,375,977 B1 * | 4/2002 | Auguste et al. | 424/447 |
| 6,964,987 B1 | 11/2005 | Auguste et al. | |
| 2005/0191248 A1 * | 9/2005 | Hunter et al. | 424/50 |
| 2005/0208114 A1 * | 9/2005 | Petito et al. | 424/445 |
| 2011/0171282 A1 * | 7/2011 | Kennedy | 424/443 |
| 2012/0247487 A1 * | 10/2012 | Llinas et al. | 128/849 |
| 2013/0018336 A1 | 1/2013 | Pernot | |

FOREIGN PATENT DOCUMENTS

| | | |
|---|---|---|
| EP | 0503029 | 9/1992 |
| EP | 0621042 | 10/1994 |
| EP | 0927051 | 7/1999 |
| EP | 1020198 | 7/2000 |
| EP | 1061965 | 12/2000 |
| EP | 1165717 | 1/2002 |
| FR | 2392076 | 12/1978 |
| FR | 2495473 | 6/1982 |
| WO | WO 92/05755 | 4/1992 |
| WO | WO 98/10801 | 3/1998 |
| WO | WO 99/27975 | 6/1999 |

* cited by examiner

WOUND DRESSING INCLUDING AGGLOMERATES OF PARTICLES SUITABLE FOR RAPIDLY GELLING OR SOLUBILIZING

The present invention concerns a novel repositionable dressing comprising an adhesive hydrocolloid mass, which wound dressing is intended for the treatment of wounds, such as exudative wounds, burns, superficial or deep dermo-epidermal lesions, which may be chronic or acute, and in particular for the treatment of blisters.

Dressings comprising hydrocolloids have been known for more than 20 years. They are composed of a backing on which is deposited an adhesive mass comprising hydrocolloids. Mention may be made, as examples, of the products sold under the names Algoplaque® by Laboratoires URGO and Comfeel® by Coloplast. Dressings comprising an adhesive mass comprising hydrocolloids, specifically intended for the treatment of blisters, are also known and are sold, for example, under the names Urgo Traitement Ampoules® by Laboratoires URGO and Compeed® by Johnson & Johnson.

In order to make possible good absorption of the exudates from the wound, these dressings comprise relatively high amounts (of the order of 20 to 50% by weight) of hydrocolloids. Preferably, these dressings are designed to be held in place without the help of an additional adhesive tape, adhering directly to the skin.

The adhesive mass of these known dressings is normally composed of a hydrophobic continuous phase in which is dispersed a noncontinuous phase of hydrocolloid particles intended to absorb the exudates from the wound.

The absorption of the exudates by the hydrocolloids causes the adhesive mass to gel, which makes it possible to painlessly remove the dressing from the wound after it has been used.

In order to provide for the maintenance over time of their absorption capacity and of their cohesion during removal, these dressings have a high initial adhesiveness. This is even truer for the dressings intended for the treatment of blisters, which have to be positioned in areas which are curved or difficult to access and which are subject to high mechanical stresses during their use.

In order to increase the adhesiveness of these dressings, work has been directed:

on the one hand, on the qualitative and quantitative composition of the adhesive masses constituting them; and on the other hand, on the shape of these dressings, in particular by giving them beveled edges.

Such dressings and their compositions are well known and are described, for example, in the documents EP 264 299, EP 503 029, EP 1 020 198 and FR 2 495 473.

However, due to their high adhesiveness, these dressings cannot be easily repositioned during their deployment on the skin of the patient. This is because the removal of these dressings is very painful as the dressing adheres to the wound or the blister, as long as it has not absorbed the exudates, which may require a relatively long time of the order of 15 minutes or more.

However, the repositioning of the dressing during its deployment is very often necessary, for example when the surface of the body on which this dressing has to be applied is not flat, and this problem is well known to nursing personnel.

In addition, these dressings are all the more difficult to deploy as they are generally very fine and, in the case of dressings intended for the treatment of blisters, small in size and as they have to be positioned in places which are difficult to access: toes, arches of the foot, heels, and the like.

Many users have already been confronted with this problem of repositioning, particularly in the case of dressings intended for the treatment of blisters, which it is also desirable to be able to reposition for reasons of unobtrusiveness and attractiveness, for example to avoid the formation of folds or to conceal the dressing behind the strap of a shoe.

Although numerous applicator systems have been developed over the last twenty years to make it easier to put on these dressings, these systems do not, however, make it possible to satisfactorily solve the problem of the repositioning and in particular there does not currently exist an ideal solution to the problem of the painless removal of an adhesive dressing immediately after a first deployment.

Under these conditions, it is an aim of the present invention to solve the novel technical problem consisting of the provision of an adhesive hydrocolloid dressing of a novel design, which can be painlessly removed immediately after it has been put on in order to be repositioned one or more times, while retaining its properties of adhesion, cohesion and absorption over time.

It has been discovered, and this constitutes the basis of the present invention, that it was possible to solve this technical problem, in a relatively simple way which can be used on the industrial scale, by modifying the surface intended to come into contact with the skin of a conventional hydrocolloid adhesive dressing by depositing thereon preconstituted particle agglomerates capable of dissolving or gelling upon contact with the exudates from the wound substantially completely and in a very short period of time, preferably of less than 10 seconds and more preferably of less than 1 second.

Thus, according to a first aspect, a subject matter of the present invention is a dressing comprising an adhesive mass comprising hydrocolloids, characterized in that the dressing comprises, on a portion at least of the surface of the adhesive mass intended to come into contact with the wound in the position of use, a plurality of agglomerates composed of particles bonded to one another, preferably according to a multilayer configuration, said particles being composed, for 90% at least and preferably 95% at least of them, of one (or more) material(s) chosen from polysaccharides, proteins and synthetic polymers, and capable of dissolving or gelling in less than 10 seconds and more preferably in less than 1 second upon contact with the exudates from the wound.

As is understood, by rapidly dissolving or gelling on contact with the exudates from the wound, the abovementioned particle agglomerates will form an intermediate layer which is not adhered to the wound immediately (at most a few seconds) after the first deployment of the dressing, thus making it possible, if need be, to painlessly remove the dressing from the wound and to reposition it.

It has been found that, despite the presence of these water-soluble or gellable particle agglomerates, the dressing retains the same adhesion profile on removal and the same absorption properties as a dressing having the same composition but not comprising these agglomerates. In particular, with these novel dressings, no migration of the exudates was observed beyond or around the part of the surface of the adhesive mass covered with the layer formed after gelling or with dissolution of the agglomerates, which might have detrimentally affected the adhesive properties or absorption and cohesion properties of the dressing by creating an absorption differential between these two areas.

According to a specific feature, these agglomerates can comprise particles of active substances which will be rapidly released and which will facilitate the healing of the blister or wound.

The dressing according to the present invention can be easily obtained by simple deposition of preformed particle agglomerates on the surface intended to come into contact with the wound of an adhesive dressing comprising hydrocolloids.

The following is a brief description of the drawings.

The adhesive masses comprising hydrocolloids capable of being used for the manufacture of the dressing in accordance with the invention are those normally used by a person skilled in the art for the manufacture of hydrocolloid adhesive dressings.

Generally, the adhesive masses of the dressings according to the invention exhibit an adhesive strength of at least 150 cN/cm and preferably of between 200 cN/cm and 8 N/cm, measured on a sheet of steel according to European standard EN 1939 (measurements at 90°, rate of 100 mm/min).

Generally, these adhesive masses will be composed of an elastomeric matrix comprising hydrocolloid particles and one (or more) compound(s) intended to confer adherence properties on said mass known under the name of "tackifier(s)".

"Elastomeric matrix" is intended here to denote a composition comprising one (or more) elastomer(s) chosen from poly(styrene-olefin-styrene) block copolymers, the olefin blocks of which can be composed of isoprene, butadiene, ethylene-butylene or ethylene-propylene units and their mixtures.

In the context of the present invention, preference will be given to poly(styrene-isoprene-styrene) triblock copolymers (abbreviation: poly(SIS)) and to the blends of poly(SIS) triblock copolymers and poly(styrene-isoprene) diblock copolymers, and in particular to the poly(SIS) having a styrene content of between 14 and 52% by weight and preferably between 14 and 30% by weight, with respect to the weight of said poly(SIS).

Such products, which are well known to a person skilled in the art, are, for example, sold by Kraton under the Kraton®D name or by Dexco Polymers LP under the Vector® name.

Mention may in particular be made, among the preferred poly(SIS) triblock copolymers, of the products sold under the names Kraton®D-1111CS, Kraton®D-1107 or Kraton®1161, Vector®4114 and Vector®4113.

Poly(styrene-butadiene-styrene) triblock copolymers can also be used in the context of the invention.

Mention may in particular be made, among these poly(styrene-butadiene-styrene) copolymers, of the product sold under the name Kraton®D-1102 by Kraton.

Preferably, the elastomers forming the elastomeric matrix will be present, in the adhesive mass of the dressings according to the invention, in an amount of 10 to 30% by weight and preferably of 15 to 25% by weight, of the total weight of the adhesive mass.

Generally, the abovementioned elastomeric matrix incorporates one (or more) hydrocolloid(s).

"Hydrocolloid" is intended here to denote any compound normally used by a person skilled in the art for its ability to absorb hydrophilic liquids, such as water, physiological saline or exudates from a wound.

Mention may be made, as example of hydrocolloid capable of being used in the context of the invention, of pectin, alginates, natural vegetable gums, such as, in particular, karaya gum, cellulose derivatives, such as, in particular, carboxymethylcelluloses and their alkali metal salts, in particular sodium or calcium salts, and synthetic polymers based on acrylic acid salts, known under the name of "superabsorbents", such as, in particular, the products sold by BASF under the name Luquasorb® 1003 or by CIBA Specialty Chemicals under the name Salcare® SC91. Of course, mixtures of these products can be used as hydrocolloids.

It should be noted that these compounds are present in the elastomeric mass and, although capable of gelling on contact with the exudates, their possible gelling can only occur after a relatively long period of time, as much as several hours, so that these compounds are not capable of solving the problem of the repositioning of the dressing.

The preferred hydrocolloids in the context of the present invention are the alkali metal salts of carboxymethylcellulose, in particular sodium carboxymethylcellulose.

The amount of hydrocolloid(s) incorporated in the elastomeric matrix will be adjusted as a function of the desired level of absorption. Generally, the amount of hydrocolloid(s) can be of the order of 2 to 50% by weight, with respect to the total weight of the adhesive mass.

In the context of the present invention, use will preferably be made of an amount of hydrocolloid(s) of between 20 and 50% by weight, with respect to the total weight of the adhesive mass, if it is desired to produce an absorbent dressing of the type of those described in the documents EP 1 061 965, EP 1 165 717 and EP 0 927 051.

The elastomeric matrix comprising hydrocolloid particles is rendered adhesive by the addition of "tackifying" products, such as those which are normally used by a person skilled in the art in the preparation of pressure-sensitive adhesives based on elastomers and in particular on poly(styrene-olefin-styrene) block copolymers. Reference may be made, for a detailed description of these products, to the documents of the state of the art mentioned above or to the work by Donatas Satas, "Handbook of Pressure Sensitive Technology", 3rd edition, 1999, pages 346 to 398.

Generally, use may be made of one (or more) tackifying product(s) which will be incorporated in the hydrocolloid mass in a broad proportion of the order of 1 to 70% by weight, with respect to the total weight of the adhesive mass, which will be determined as a function of the nature and relative proportion of the other constituents of this mass, in order to obtain the adhesiveness desired for the final composition.

Preferably, the tackifying product(s) will represent from 10 to 40% by weight, of the total weight of the hydrocolloid mass.

The tackifying products capable of being used in the context of the present invention can be chosen from tackifying resins, polyisobutylenes of low molecular weight, polybutenes of low molecular weight or their mixtures.

Mention may be made, among the tackifying resins capable of being used according to the invention, of modified terpene or polyterpene resins, rosin resins, hydrocarbon resins, mixtures of cyclic, aromatic and aliphatic resins, and the like, or mixtures of these resins.

Such products are sold, for example:
  by Goodyear under the Wingtack® name, such as, in particular, the synthetic resin formed of $C_5/C_9$ copolymers (Wingtack® 86) or the resin based on synthetic polyterpene (Wingtack® 10);
  or by Hercules under the Kristalex® name, such as, in particular, the resin based on a-methylstyrene (Kristalex® 3085).

These tackifying resins can be used alone or as a mixture with other tackifiers, preferably in a proportion of 20 to 50% by weight and more particularly of 25 to 35% by weight, with respect to the total weight of the adhesive mass.

Mention may be made, among the polybutenes of low molecular weight capable of being used according to the invention, for example, of the products sold by the company BP Chimie under the Napvis® name, in particular the product sold under the name Napvis® 10.

These polybutenes can be used alone or as a mixture with other tackifiers, preferably in a proportion of 5 to 30% by weight and more particularly of 8 to 15% by weight, with respect to the total weight of the adhesive mass.

Mention may be made, among the polyisobutylenes of low molecular weight capable of being used according to the invention, of the polyisobutylenes having a molecular weight of the order of 40 000 to 80 000 daltons, such as, for example, the products sold by BASF under the Oppanol® name and in particular the products sold under the names Oppanol®B12 and Oppanol®B15.

These polyisobutylenes can be used or as a mixture with other tackifiers, preferably in a proportion of 5 to 30% by weight and more particularly 8 to 15% by weight, with respect to the total weight of the adhesive mass.

Various additional compounds can be added to the elastomeric matrix comprising the abovementioned tackifying and hydrocolloid compounds in order to obtain hydrocolloid adhesive masses which exhibit optimized properties of elasticity, adhesion, stability over time and cohesion.

Such compounds are, for example, stabilizers, such as, in particular, antioxidants, plasticizers, such as, in particular, polybutenes or plasticizing oils, or agents which make it possible to improve the cohesion, such as, in particular, butyl rubbers or polyisobutylenes of high molecular weight.

Mention may be made, among the polyisobutylenes of high molecular weight capable of being used according to the invention to improve the cohesion of the adhesive mass, of polyisobutylenes having a molecular weight of the order of 400 000 to 2 000 000 daltons, such as, for example, the products sold by BASF under the names Oppanol®B12 SFN or Oppanol®B30 SF.

These polyisobutylenes of high molecular weight can be used alone or as a mixture, preferably in a proportion of 2 to 20% by weight and more particularly of 5 to 15% by weight, with respect to the total weight of the adhesive mass.

"Stabilizer" is intended here to denote any compound capable of providing stability, with regard to oxygen (antioxidant), heat, ozone and ultraviolet radiation, to the compounds used in the formulation of the adhesive hydrocolloid masses, in particular tackifying resins and block copolymers. These stabilizing compounds are well known and can be used alone or as a mixture.

Mention may be made, among the antioxidizing compounds capable of being used according to the invention, of phenolic antioxidants, such as, for example, the products sold by Ciba-Geigy under the names Irganox®1010, Irganox® 565 and Irganox® 1076, and sulfur-comprising antioxidants, such as, for example, zinc dibutyldithiocarbamate, sold by Akzo under the name Perkacit®ZDBC.

These compounds can be used alone or as a mixture, preferably in a proportion of 0 to 2% by weight and more particularly 0.1 to 0.6% by weight, with respect to the total weight of the hydrocolloid mass.

In the context of the present invention, use will preferably be made of the combination of Irganox®1010 and Perkacit®ZDBC.

Mention may be made, among the plasticizing compounds capable of being used according to the invention, of the plasticizers normally used by a person skilled in the art in the preparation of hydrocolloid adhesive masses and in particular polybutenes, such as, for example, the products sold by BP Chemicals under the name Napvis® 10, plasticizing oils or phthalate derivatives, such as dioctyl phthalate.

The use of plasticizing oils is particularly preferred in the context of the present invention.

"Plasticizing oil" is intended here to denote the mineral or vegetable oils commonly employed by a person skilled in the art to plasticize the block copolymers of the styrene-olefin-styrene type used in the composition of hydrocolloid adhesive masses.

These mineral oils are generally composed of mixtures in variable proportions of compounds of paraffinic, naphthenic or aromatic nature.

Mention may be made, among the plasticizing oils capable of being used according to the invention, of the products sold by Shell under the Ondina® and Risella® names, which are composed of mixtures based on naphthenic and paraffinic compounds, or under the Catenex® name, which are composed of mixtures based on naphthenic, aromatic and paraffinic compounds.

In the context of the present invention, use will preferably be made of the mineral plasticizing oil sold under the name Ondina®68.

These plasticizing compounds can be used alone or as a mixture, preferably in a proportion of 5 to 20% by weight and more particularly of 7 to 15% by weight, with respect to the total weight of the hydrocolloid mass.

The hydrocolloid adhesive mass of the dressings according to the invention can also comprise one or more surface-active compound(s) in an amount of less than or equal to 10% by weight, preferably of less than or equal to 5% by weight, with respect to the total weight of the hydrocolloid mass.

A preferred surface-active compound in the context of the present invention is the compound sold under the AcResin® name.

Another preferred surface-active compound in the context of the present invention is polysorbate 80, such as, for example, the product sold by Seppic under the name Montanox® 80.

In the context of the present description, the expression "particle agglomerate" is intended to denote an assembly of particles which are small in size, that is to say having a mean size of between 500 nm and 1000 μm, preferably of between 1 μm and 500 μm, which are bonded together, preferably according to a multilayer arrangement, for example in the raspberry form.

Each agglomerate generally has a mean size of between 5 and 2000 μm and will thus be composed of approximately 10 to 10 000 particles, preferably of approximately 100 to 1000 particles.

Such particle agglomerates can be prepared, in a way known per se, by wet granulation processes, such as, in particular, by spray drying or in a fluidized air bed, generally using water or an aqueous mixture as binder.

Generally, the particles forming the agglomerates are composed predominantly, that is to say for 90% at least and preferably for 95% at least of them, of a material chosen from polysaccharides, proteins and synthetic polymers, and capable of dissolving or gelling in less than 10 seconds and more preferably in less than 1 second upon contact with the exudates from the wound.

The expression "material capable of dissolving" is intended to denote any material capable of dissolving in the exudates from the wound with the formation of a homogeneous solution.

The expression "material capable of gelling" is intended to denote any material capable of forming a gel upon contact with the exudates from the wound, i.e. a substance exhibiting a viscosity greater than that of water, for example greater than $10^{-3}$ Pa·s and preferably greater than $10^{-2}$ Pa·s.

Mention may be made, among the polysaccharides capable of being used according to the invention, of starch, modified starches, maltodextrin, gums, such as, in particular, gum arabic, xanthan gum or acacia gum, pullulan, dextrans, cellulose, cellulose derivatives, such as, in particular, methylcellulose, hydroxypropylmethylcellulose, hydroxypropylcellulose or hydroxyethylcellulose, sugars, pectin, alginates, carragheenans or agar.

Excellent results have been obtained using particles of maltodextrin, which thus constitutes a preferred material for the implementation of the invention.

Mention may be made, among the proteins capable of being used according to the invention, of gelatin, albumin, collagen and casein.

Mention may be made, among the synthetic polymers capable of being used according to the invention, of superabsorbent polymers, such as, in particular, polyacrylates, and also water-soluble synthetic polymers, such as, in particular, polyvinyl alcohol.

The agglomerates used in the context of the present invention can be composed of particles which are different in nature, depending on the degree of solubility desired, the mechanical strength desired or the temperature stability desired.

According to a specific embodiment of the invention, the agglomerates comprise one (or more) active substance(s).

In the case where a plurality of active substances is used, these active substances can be incorporated either individually in separate agglomerates or in the form of a mixture within one and the same agglomerate.

The active substances capable of being used in the context of the present invention can be chosen from antifungals, antimicrobials or antibacterials, such as silver sulfadiazine, pH regulators, healing accelerators, such as hyaluronic acid, vitamins, moisturizing agents, trace elements, local anesthetics, odor trappers, menthol, methyl salicylate, hormones, anti-inflammatories and the mixtures of these compounds.

A preferred active substance in the context of the invention is hyaluronic acid.

According to the invention, the agglomerates are positioned uniformly or nonuniformly at the surface of the hydrocolloid adhesive mass intended to come into contact with the wound. In other words, these agglomerates will not be present inside the hydrocolloid adhesive mass.

Generally, the agglomerates will cover between 5 and 90% and preferably between 10 and 60% of the surface of the adhesive mass coming into contact with the wound, according to the application envisaged. Thus, the degree of covering of the surface of the adhesive mass coming into contact with the wound will be of the order of 10 to 50% for a dressing intended for the treatment of blisters and of the order of 20 to 70% for a dressing intended for the treatment of bedsores or ulcers.

These agglomerates can be incorporated in the dressing in accordance with invention by any process which makes possible their deposition at the surface of the hydrocolloid adhesive mass.

For example, this operation can advantageously be carried out by dusting the agglomerates over the surface of the hydrocolloid adhesive mass using a powder dispenser known to a person skilled in the art.

According to a preferred embodiment of the invention, the preformed agglomerates will be positioned solely on the area of the dressing intended to come into contact with the area of the wound to be treated.

For example, the agglomerates can be deposited on the areas intended to constitute the central part of the dressings or distributed evenly or unevenly at the surface of these areas.

The agglomerates can be deposited according to any geometrical shape, for example a square, rectangular, oval or striated shape. To this end, the deposition operation can be carried out using a stencil which makes it possible to obtain the desired shape.

The amount of agglomerates deposited can vary within wide proportions and will generally be between 5 and 500 grams per square meter of dressing, preferably between 10 and 150 $g/m^2$.

The dressings of the invention can be of different types but will preferably comprise a backing.

The adhesive mass carrying the agglomerates can be complexed to a backing of the type of those used in the dressings sold by Laboratoires Urgo under the Algoplaque® names or by Convatec under the Duoderm® name or also by Coloplast under the Comfeel® name. Such dressings are described in the documents FR 2 392 076, FR 2 495 473, WO 98/10801 and EP 264 299.

Generally, the choice of the backing will be made as a function of the properties required (leaktightness, elasticity, and the like) in the desired application.

Thus, the dressing according to the invention can comprise a backing, such as a film formed of one or more layers and with a thickness which can vary from 5 to 150 µm, a nonwoven or a foam having a thickness of 10 to 500 µm, onto which the hydrocolloid adhesive mass has been coated in a continuous or noncontinuous fashion.

These backings based on synthetic or natural materials are well known to a person skilled in the art.

Mention may thus be made, among the backings in the form of a foam which can be used in the context of the invention, of polyethylene, polyurethane or PVC foams, for example.

Mention may be made, among the nonwoven backings which can be used in the context of the invention, of nonwovens made of polypropylene, polyethylene, polyurethane, polyamide, or polyester, for example.

In the context of the present invention, preference will be given to the use of backings in the form of films, in particular polyurethane films, such as, for example, the films sold by Smith and Nephew under the Lasso® reference which are produced from polyurethane sold by BF Goodrich under the Estane® name; low-density polyethylene films, such as, for example, the films sold by Sopal; films based on thermoplastic polyether/polyester copolymer, such as, for example, products sold by Dupont de Nemours under the Hytrel® name; or complex films combining a polyurethane film and a nonwoven.

Figure 1:
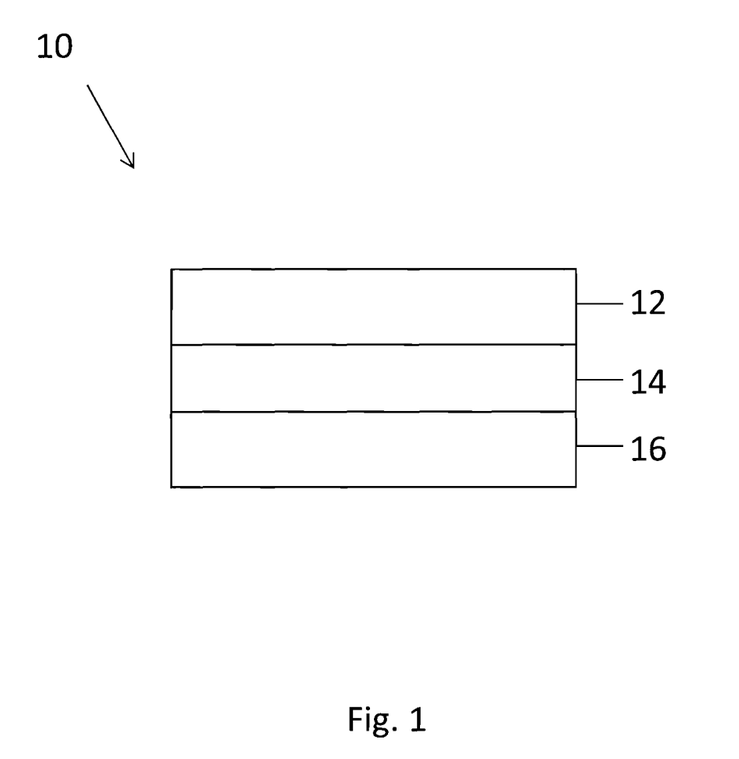
FIG. 1 shows a schematic illustration of one embodiment of the disclosed wound dressing.

With reference to FIG. 1, in an alternative embodiment of the invention, a dressing 10 can comprise an absorbent layer 14 positioned between a backing 16 and an adhesive hydrocolloid mass 12. This absorbent layer 14 can be composed of any type of absorbent material, such as, for example, a foam (such as, in particular, a polyurethane foam), a nonwoven, a superabsorbent polymer layer or a combination of these materials.

The dressings produced from the hydrocolloid adhesive mass according to the invention can be provided in any geometrical shape, for example square, rectangular, circular or oval. Likewise, they can have any size and the latter will be adapted as a function of the surface of the part to be treated or protected. For example, a dressing intended for the treatment of blisters will be provided in a rectangular form with a length of approximately 7 cm and a width of approximately 4 cm, while a dressing intended for the treatment of ulcers will be provided in a square form with a side length of 10 cm.

In practice, the surface of the hydrocolloid adhesive mass carrying the agglomerates can be covered with a protective film intended to be removed, for example by peeling, before the deployment of the dressing on the wound and/or on the skin.

The assembly thus formed can itself be wrapped in a leak-tight protection formed, for example by means of polyethylene/aluminum complexes or in blister packs.

The invention will be illustrated by the following nonlimiting examples.

EXAMPLE 1

Preparation of a Standard Hydrocolloid Dressing

A hydrocolloid adhesive mass was prepared composed of the following compounds (amount expressed by weight per 100 grams of mass).

| No. | Compound | Amount (by weight per 100 grams) |
|---|---|---|
| 1 | Elastomer<br>Styrene-Isoprene-Styrene/Styrene-Isoprene block copolymer (sold under the name Vector ® 4114A by Dexco Polymers LP) | 14.144 |
| 2 | Cohesion-improving agent<br>Polyisobutene (sold under the name Oppanol ® B12SFN by BASF) | 3.536 |
| 3 | Plasticizer<br>Mineral oil (sold under the name Ondina ® 933 by Shell) | 12.376 |
| 4 | Surfactant<br>UV-crosslinkable acrylic ester copolymer (sold under the name AcResin ® A258UV by BASF) | 6.542 |
| 5 | Tackifying resin<br>Synthetic hydrocarbon resin (sold under the name Wingtack ® 86 by Safic Alcan) | 26.521 |
| 6 | Hydrocolloid<br>Carboxymethylcellulose (sold under the name CMC Blanose ® 7H4XF by Hercules) | 35.714 |
| 7 | Surfactant<br>Polysorbate 80 (sold under the name Montanox ® 80 by Seppic) | 0.460 |
| 8 | Antioxidant<br>Zinc dibutyldithiocarbamate (sold under the name Perkacit ® ZDBC by Flexsys (distributor Arnaud)) | 0.354 |
| 9 | Antioxidant<br>Pentaerythritol tetrakis(3-(3,5-di(tert-butyl)-4-hydroxyphenyl)propionate) (sold under the name Irganox ® 1010 by Ciba Speciality Chemicals) | 0.354 |

This hydrocolloid adhesive mass was prepared by carrying out the following process:

Compounds 1, 2, 3, 8 and 9 were introduced into a Z-arm blender at a set temperature of 140° C.

Compound 4 was added at the 30th minute.
Compound 7 was added at the 40th minute.
Compound 5 was added at the 45th minute.
Compound 6 was added at the 60th minute.
The blender was emptied at the 80th minute.

The adhesive hydrocolloid mass was heated to a temperature of the order of 110 to 130° C. and then coated on to a backing composed of a polyurethane film having a thickness of 30 μm. The complex formed of the hydrocolloid mass and backing was subsequently cut into individual dressings covered, on the free adhesive hydrocolloid surface, with protective tabs made of silicone polyester.

EXAMPLE 2

Preparation of a Dressing According to the Invention a) Preparation of Maltodextrin-Based Agglomerates Maltodextrin-based agglomerates were prepared by spraying an aqueous solution over a maltodextrin powder in a fluidized air bed granulator.

After drying at 80° C. during the duration of incorporation by spraying, agglomerates were obtained having a general structure of "raspberry" type exhibiting a mean dimension of 400 μm approximately.

b) Deposition of Agglomerates at the Surface of a Hydrocolloid Adhesive Mass

The adhesive hydrocolloid mass prepared in example 1 was heated to a temperature of the order of 110 to 130° C. and then coated on to a backing composed of a polyurethane film having a thickness of 30 μm. The complex formed by the hydrocolloid adhesive mass and the polyurethane film was cut into individual dressings.

Maltodextrin-based agglomerates were subsequently deposited on the free surface (not bonded to the backing) of the hydrocolloid adhesive mass.

These agglomerates were deposited in an amount of between 100 and 150 g/m$^2$.

These agglomerates were deposited at the centre of the dressing, covering substantially 15% of the free surface of the adhesive mass.

The surface of the adhesive hydrocolloid mass carrying the agglomerates was covered with protective tabs made of silicone polyester.

EXAMPLE 3

Demonstration of the Properties of the Dressing in Accordance with the Invention The adhesive strength of the dressings as prepared in examples 1 and 2, after contact with physiological saline to simulate the exudation from a wound, was measured in order to evaluate the difference in behavior on removal between a dressing comprising a conventional hydrocolloid adhesive mass (example 1) and a dressing according to the invention comprising a hydrocolloid adhesive mass, the surface of which intended to come into contact with the skin carries agglomerates (example 2).

To this end, use was made of the "probe tack" method, which aims to measure the detachment of a cylindrical probe applied to an adhesive with a pressure stress $P_0$ for a given time t under predetermined temperature and humidity conditions.

Equipment

Figure 2:
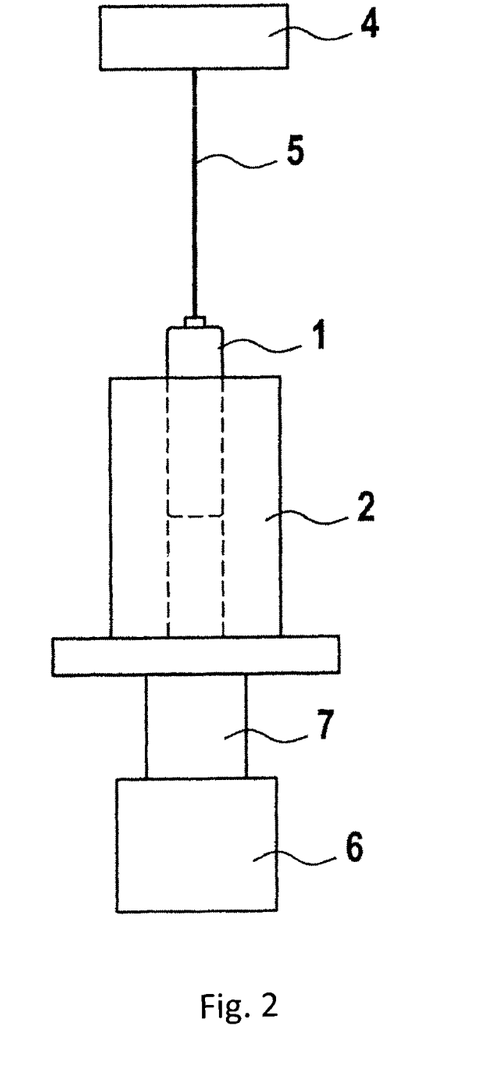
FIG. 2 shows a schematic illustration of an example of a device for evaluating a wound dressing.

More specifically, this method was carried out using the device represented in FIG. 2.

This device is essentially composed:
of a cylindrical probe 1 exhibiting a finely polished end capable of moving longitudinally (from the bottom upwards in the example represented) through a probe guide 2 composed of a cylinder pierced in its center with a free hole which makes possible the free frictionless passage of the probe;
of an electronic dynamometer comprising a movable gripping element 4 which can be connected to the probe 1 via a small chain 5 and a base 6 on which a plate 7 can be fitted, said dynamometer being in addition connected to a system for acquiring and recording data, such as in particular the rate of descent of the probe, the contacting pressure of the probe on the adhesive, the contact time between the probe and adhesive and the rate of rise of the probe.

Samples

Standard Dressing

A substantially square dressing with a side length of 20 cm was prepared by following the experimental protocol of example 1.

This dressing was covered with a double-sided adhesive tape on the face forming the backing. A pressure roll was employed in order to cause said tape to adhere well to the surface of the dressing.

Circular samples with the same surface area as the probe were cut from the assembly thus formed by the dressing and the abovementioned adhesive tape using a circular hollow punch with a diameter of 30 mm.

Dressing According to the Invention

A second set of samples of the same nature and of the same size was prepared.

Maltodextrin-based agglomerates, such as those prepared in example 2, were deposited on the surface of these samples (the excess agglomerates having been removed in order to uniformly cover the surface of the sample).

Procedure:

The plate 7 was fitted to the base 6 of the dynamometer.
The small chain 5 of the probe was attached to the movable gripping element 4 of the dynamometer.
The probe 1 was cleaned with a solvent (this operation being repeated before each measurement).
A sample (double-sided side) as prepared above was applied to the probe.
50 μl of physiological saline were deposited on the plate 7 in the middle of the area delimited by the probe guide.
The parameters of the dynamometer (rate of descent, contacting pressure, contact time and rate of rise) were programmed.
The measurement was carried out by performing the following operations: descent of the probe, bringing the adhesive sample and the physiological saline into contact.
The detachment force was recorded in kPa and was translated into tear-off stress S according to the relationship:

$$S = F/A$$

where F=Force expressed in N and A=Area expressed in m².

Parameters of the Test:

Application stress: 1.7 kPa (aluminum probe with a weight of 121 g and a diameter of 30 mm)
Test rate: 300 mm/min
Pressure roll: 4 kg
Contact time: 1 s The measurements were carried out on 3 samples of each of the standard dressing and dressing according to the invention and repeated 6 times.

Results:

The results of the measurements thus carried out, expressed in kPa, have been given in table I.

TABLE I

| Test No. | Example 1 | Example 2 |
|---|---|---|
| 1 | 138.8 | 30.1 |
| 2 | 182.8 | 25.8 |
| 3 | 171.2 | 27.7 |

TABLE I-continued

| Test No. | Example 1 | Example 2 |
|---|---|---|
| 4 | 160.7 | 34.5 |
| 5 | 134.4 | 21.7 |
| 6 | 194 | 27.7 |

Observations of the Behavior of the Dressings According to Examples 1 and 2 in the Presence of Physiological Saline

| Conditions | Observations after contact with physiological saline |
|---|---|
| Example 1 + 50 μl of physiological saline | Complete gelling after 15 minutes |
| Example 2 + 50 μl of physiological saline | Dissolution in one second |

CONCLUSIONS

The virtually complete dissolution of the agglomerates is very fast (1 s).

The "probe tack" test has made it possible to state that the adhesive strength on removal of the hydrocolloid adhesive dressing according to the invention is much lower than that of a standard agglomerate-free dressing.

When the hydrocolloid adhesive mass of the dressing carries agglomerates, the adhesive strength on removal of the dressing becomes minimal, indeed even virtually zero, when it comes into contact with physiological saline, even in a very small amount.

Thus, a dressing according to the invention, that is to say comprising a hydrocolloid adhesive mass carrying agglomerates of water-soluble or gellable particles on its surface intended to come into contact with the wound, can be easily repositioned after a first application, this being the case in the seconds which follow said first application.

The invention claimed is:

1. A wound dressing, comprising:
   an adhesive mass comprising hydrocolloids,
   wherein the dressing comprises, on a portion at least of a surface of the adhesive mass intended to come into contact with a wound in a position of use, a plurality of agglomerates composed of particles bonded to one another, said particles comprising 90% or more of at least one selected from the group consisting of a polysaccharide, a protein and a synthetic polymer, and the agglomerates being configured to dissolve or gel in less than 10 seconds on contact with the exudates from the wound,
   wherein the hydrocolloids are present in an amount of 20 to 50% by mass with respect to the total weight of the adhesive mass, and
   wherein the particles are bonded in a multi-layer configuration.

2. The wound dressing as claimed in claim 1, wherein the particles have a mean size of 500 nm to 1000 μm.

3. The wound dressing as claimed in claim 1, wherein the agglomerates have a mean size of 5 to 2000 μm.

4. The wound dressing as claimed in claim 1, wherein the agglomerates are present in an amount of 5 to 500 g per m² of the dressing.

5. The wound dressing as claimed in claim 1, wherein the agglomerates cover from 10 to 60% of the surface of the adhesive mass that is intended to come into contact with the wound in the position of use.

6. The wound dressing as claimed in claim 1, wherein the polysaccharide is at least one selected from the group consisting of a modified starch, maltodextrin, a gum, pullulan, a dextran, cellulose, a cellulose derivative, a sugar, pectin, an alginate, a carragheenan and agar.

7. The wound dressing as claimed in claim 6, wherein the gum is at least one selected from the group consisting of gum arabic, xanthan gum and acacia gum.

8. The wound dressing as claimed in claim 6, wherein the cellulose derivative is at least one selected from the group consisting of methylcellulose, hydroxypropylmethylcellulose, hydroxypropylcellulose and hydroxyethylcellulose.

9. The wound dressing as claimed in claim 1, wherein the material constituting the particles is maltodextrin.

10. The wound dressing as claimed in claim 1, wherein the agglomerates comprise at least one active substance selected from the group consisting of a healing accelerator, an antifungal, an antimicrobial, an antibacterial, a moisturizing agent, a local anesthetic, and an anti-inflammatory.

11. The wound dressing as claimed in claim 1, wherein the agglomerates comprise hyaluronic acid as an active substance.

12. The wound dressing as claimed in claim 1, further comprising a backing.

13. The wound dressing as claimed in claim 1, further comprising an absorbent layer situated between the backing and the adhesive mass.

14. The wound dressing as claimed in claim 1, wherein the particles comprise 95% or more of at least one selected from the group consisting of a polysaccharide, a protein and a synthetic polymer.

15. The wound dressing as claimed in claim 1, wherein the agglomerates are configured to dissolve or gel in less than 1 second.

16. The wound dressing as claimed in claim 1, wherein the particles have a mean size of between 1 µm to 500 µm.

17. The wound dressing as claimed in claim 1, wherein the agglomerates are present in an amount of 10 to 150 g per $m^2$ of the dressing.

18. The wound dressing as claimed in claim 1, wherein the protein is at least one selected from the group consisting of gelatin, albumin, collagen and casein.

19. The wound dressing as claimed in claim 1, wherein the synthetic polymer is a superabsorbent synthetic polymer.

20. The wound dressing as claimed in claim 19, wherein the superabsorbent synthetic polymer is a polyacrylate.

21. The wound dressing as claimed in claim 1, wherein the synthetic polymer is a water-soluble synthetic polymer.

22. The wound dressing as claimed in claim 21, wherein the water-soluble synthetic polymer is polyvinyl alcohol.

* * * * *